United States Patent [19]

Horton et al.

[11] 4,427,664
[45] Jan. 24, 1984

[54] 2'HALO DERIVATIVES OF DAUNOMYCIN, DESMETHOXY DAUNOMYCIN, ADRIAMYCIN AND CARMINOMYCIN

[75] Inventors: Derek Horton; Waldemar Priebe, both of Columbus, Ohio

[73] Assignee: The United States of America as represented by the Department of Health and Human Services, Washington, D.C.

[21] Appl. No.: 408,942

[22] Filed: Aug. 17, 1982

Related U.S. Application Data

[63] Continuation of Ser. No. 268,623, May 29, 1981, abandoned.

[51] Int. Cl.³ .................. A61K 31/71; C07H 15/24
[52] U.S. Cl. ..................................... 424/180; 536/6.4
[58] Field of Search ...................... 536/6.4; 424/180

[56] References Cited

U.S. PATENT DOCUMENTS 4,201,773  5/1980  Horton et al. ................. 536/6.4

Primary Examiner—Johnnie R. Brown
Attorney, Agent, or Firm—John S. Roberts, Jr.

[57] ABSTRACT

The compounds are derived from aglycons which may be daunomycin, desmethoxy daunomycin, adriamycin and carminomycin. A preferred compound is

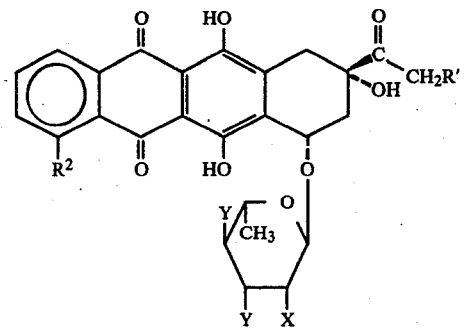

(1) R' = H; R² = OMe; X; Y
(2) R' = OH; R² = OMe; X; Y
(3) R' = H; R² = H; X; Y
(4) R' = H; R² = OH; X; Y
where X = I, Cl, Br, or F and Y = OH or AcO(acetoxy)

(1) R'=H; R²=OMe; X; Y
(2) R'=OH; R²=OMe; X; Y
(3) R'=H; R²=H; X; Y
(4) R'=H; R²=OH; X; Y where
X=I, Cl, Br, or F and
Y=OH or AcO (acetoxy)

where Y is AcO or OH and R'=H and R²=OMe.

These compounds are effective showing high anti-leukemic activity against P388 murine leukemia.

12 Claims, No Drawings

2'HALO DERIVATIVES OF DAUNOMYCIN, DESMETHOXY DAUNOMYCIN, ADRIAMYCIN AND CARMINOMYCIN

This is a continuation of application Ser. No. 268,623, filed May 29, 1981, now abandoned.

The invention described herein was made in the course of work under a grant or award from the United States Department of Health and Human Services.

This invention relates to compounds showing high antileukemic activity against P388 murine leukemia.

These compounds are coupled products of aglycon selected from daunomycinone, desmethoxy daunomycinone, adriamycinone and carminomycinone. These compounds are coupled at the 0–7 position of the aglycon with a 2 substituted halo pyranose or furanose ring structure of sugar which are pentose or hexose varieties. Preferred are α-L-manno or —talo hexopyranose or the sugar, which sugar isomers particularly sustain or potentiate the biological activity of the coupled compound.

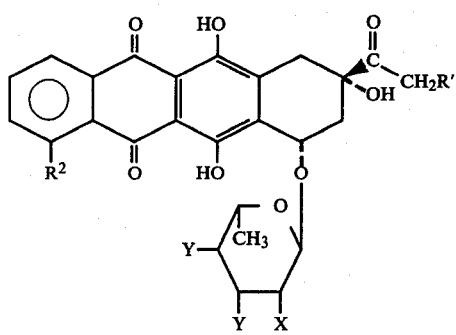

(1) R' = H; R² = OMe; X; Y
(2) R' = OH; R² = OMe; X; Y
(3) R' = H; R² = H; X; Y
(4) R' = H; R² = OH; X; Y
where X = I, Cl, Br, or F and Y = OH or OAc(acetoxy)

(1) R'=H; R²=OMe; X; Y
(2) R'=OH; R²=OMe; X; Y
(3) R'=H; R²=H; X; Y
(4) R'=H; R²=OH; X; Y
where
X=I, Cl, Br, or F and
Y=OH or OAc (acetoxy)

The compounds which are the subject of this invention are closely related in structure to natural products illustrated by daunorubicin (daunomycin), desmethoxy daunorubicin, adriamycin, and carminomycin. These compounds have shown antibiotic and antileukemic activity.

The structure of the new compounds is given in the formula above. Daunomycinone is coupled at the 7 position with a 2 halo substituted sugar and in similar fashion there may be coupled adriamycinone, carminomycinone, and desmethoxy daunomycinone. The anthracycline compound or fraction which participates in the coupling is termed an aglycon. It is noted that aglycon may be defined as a non-sugar hydrolytic product of a glycoside.

Preferred structures embodying the sugar portion are 7-O-(3,4-di-O-acetyl-2,6-dideoxy-2-iodo-d-L-mannohexopyranosyl)daunomycinone (NSC-331962) and 7-O-(3,4-di-O-acetyl-2,6-dideoxy-2-iodo-α-L-talo-hexopyranosyl)daunomycinone (NSC-327472).

PRIOR ART STATEMENT

U.S. Pat. No. 4,201,773 Horton et. al.

U.S. Pat. No. 4,058,519 Arcamone et al teaches adriamycin derivatives and reactive intermediates, for example, 1-halo-2,3,6-trideoxy-3-trifluoroacetamido-4-trifluoroacetoxy-α-L-lyxo or arabino) hexopyranoses.

U.S. Pat. No. 4,046,878 Patelli et al indicates that the reaction proceeds from daunomycin analogs and uses as a sugar the 1-chloro-2,3,6-trideoxy-3-trifluoroacetamido-4-trifluoroacetoxy-α-L-lyxo pyranose.

Additionally, the following patents are of interest: U.S. Pat. No. 3,590,028 Arcamone et al, U.S. Pat. No. 3,803,124 Arcamone et al, U.S. Pat. No. 4,067,968 Lazzari et al, U.S. Pat. No. 4,067,969 Penco et al, British Pat. No. 1,161,278, and British Pat. No. 1,217,133.

Fuchs et al, Carbohydrate Research, 57 (1977), C36–C39.

Cheung et al, Carbohydrate Research, 58 (1977), 139–151.

Horton et al, Carbohydrate Research, 77 (1979), C8–C11.

THE SUGARS

The compounds of the present invention differ from the natural products as found in nature in that halogen has been introduced in the 2' position in the basic hexopyranose structure. Of the halogens, iodo is presently preferred but bromo, chloro, and fluoro may be utilized. In the present examples, the 3'-amino has been replaced by a hydroxyl group or an acetyl group and the 4' position may also be hydroxyl or acetyl. The preferred ring structure may be pyranose or furanose and the sugar chain may be hexose or pentose.

α-L-manno hexopyranose (NSC-331962) and α-L-talo hexopyranose (NSC-327472) were tested in vivo against P388 lymphocytic leukemia in mice, with α-L-manno hexopyranose showing higher activity.

THE BIOLOGICAL EFFECT

The anthracycline antibiotics daunorubicin, adriamycin, and carminomycin are potent and clinically useful antitumor agents. Their scarcity and certain undesirable side effects common to many antitumor drugs (such as bone-marrow damage, stomatitis, and alopecia), but, in particular, a cumulative, dose-related cardiotoxicity, have limited their broader utilization in chemotherapy.

Derivatives of the natural products which are set out in this invention as well as several semi-synthetic anthracyclines have been prepared and some of these appear to display significant antitumor activity in animals with less toxicity than the parent natural products.

In particular the compound 7-O-(3,4-di-O-acetyl-2,6-dideoxy-2-iodo-α-L-manno-hexopyranosyl)daunomycinone (NSC-331962) was prepared and is a compound identical to daunorubicin except for the introduction of iodo at the 2' position and replacement of the amino function in the sugar moiety by a hydroxyl group.

In addition, as an additional series of compounds which does contain the amino function in the sugar moiety, the following compounds are disclosed below

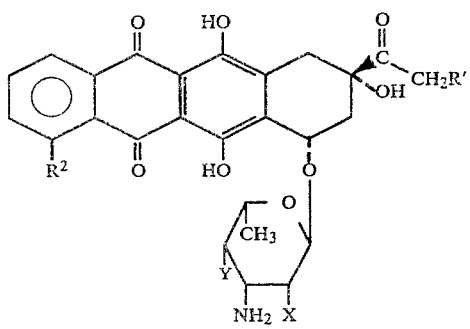

(1) R' = H; R² = OMe; X; Y
(2) R' = OH; R² = OMe; X; Y
(3) R' = H; R² = H; X; Y
(4) R' = H; R² = OH; X; Y
where: X = I, Cl, Br, or F and Y = OH or OAc(acetoxy)

(1) R'=H, R²=OMe; X; Y
(2) R'=OH; R²=OMe; X; Y
(3) R'=H, R²=H; X; Y
(4) R'=H, R²=OH; X; Y
where:
X=I, Cl, Br, or F and
Y=OH or OAc (acetoxy)
and additionally their 4'-epimers.

Certain compounds included in this invention have shown superior results when tested against P388 mouse leukemia by standard tests such as are set out in Protocol 11 of the Cancer Chemotherapy Reports of May 24, 1972, National Institutes of Health. Values for the 7-O-(3,4-di-O-acetyl-2,6-dideoxy-2-iodo-α-L-manno-hexopyranosyl)daunomycinone (NSC 331962) ranged from T/C of 247 at 50 mg, 188 at 25 mg, to 140 at 6.25 mg against P388 mouse leukemia in tests extending up to 22 days.

GENERALIZED METHOD

In general, the present preparation calls for the aglycon, for example, daunomycinone, to be reacted in about equimolar parts with the sugar, for example, 3,4-di-O-acetyl-L-rhamnal, in a non-aqueous mixture of dry acetonitrile and tetrahydrofuran. The reaction was done in the cold and an iodonating agent, such as N-iodosuccinimide, was added together with a solvating agent such as dichloromethane. Product was recovered by chromatography isolated and crystallized from a hydrocarbon mixture, such as acetone and hexane. The product introduced a halogen (iodine) at the 2 position of the sugar molecule.

Thin layer chromatography was performed on precoated plastic sheets (0.2 mm) and glass plates (0.25 mm) coated with Silica Gel 60F-254 (E. Merck, Darmstadt, G.F.R.). Column chromatography was performed with Silica Gel 60 (230–400 mexh) (E. Merck, Darmstadt, G.F.R.). Melting points were determined with a Thomas-Hoover apparatus and are uncorrected. I.R. spectra were recorded with a Perkin-Elmer 457 grating spectrophotometer. Optical rotations were measured with a Perkin-Elmer 141 polarimeter. ¹H-N.m.r. spectra were recorded at 200 MHz for solutions in chloroform-d with a Bruker WP-200 instrument. ¹³C-N.m.r. spectra were recorded at 22.115 MHz with a Bruker WP-80 instrument, with chloroform-d as solvent. Chemical shifts refer to an internal standard of tetramethylsilane ($\delta = 0.00$).

EXAMPLE 1

Preparation of 7-O-(3,4-di-O-acetyl-2,6-dideoxy-2-iodo-α-L-manno-hexopyranosyl)daunomycinone (NSC 331962)

Daunomycinone (604.4 mg, 1.52 mmol) and 3,4-di-O-acetyl-L-rhamnal (355 mg, 1.57 mmol) were dissolved in a mixture of dry acetonitrile (12 mL) and tetrahydrofuran (5 mL). The mixture was cooled to 0° C. and vigorously stirred while N-iodosuccinimide (512 mg, 2.27 mmol) was added. The resulting mixture was stirred for 15 minutes at the same temperature, and then the ice bath was removed and the mixture was kept overnight at room temperature. T.L.C. (4:1 benzene—acetone) showed presence of one major spot. Dichloromethane (25 mL) was then added and the resultant solution was shaken twice with 10% aqueous sodium thiosulfate (20 mL), and then washed with water (twice, 30 mL) and dried with magnesium sulfate. The mixture was filtered and the filtrate evaporated under diminished pressure, and the product immediately chromatographed on silica gel with 8:1 benzene—acetone as eluant. The fraction containing pure 7-O-(3,4-di-O-acetyl-2,6-dideoxy-2-iodo-α-L-mannohexopyranosyl)-daunomycinone (Compound 1) was isolated and the product crystallized from acetone—hexane; yield 412.3 mg (37%), m.p. 142°–144°, $[\alpha]_D^{27} + 69.9°$ (c 0.02, chloroform); $\nu_{max}^{KBr}$ 3490 (OH), 1747 (O-acetyl), 1714 (C-acetyl) 1618 and 1573 (chelated quinone), 1377, 1284, 1235, 1212, 1118, 1069, 1049 and 992 cm⁻¹; ¹H-n.m.r.: $\delta$13.99, 13.23 (s, 1H, HO-6, HO-11), 8.03 (dd, 1H, $J_{1,2}$ 7.7, $J_{1,3}$ 0.9 Hz, H-1), 7.78 (apparent t, 1H, H-2) 7.39 (dd, 1H, $J_{2,3}$ 8.6 Hz, H-3), 5.77 (bs, 1H, H-1'), 5.25 (m, 1H, H-7), 5.18 (t, 1H, H-4'), 4.59 (dd, 1H, $J_{1',2'}$ 1.3, $J_{2',3'}$ 4.3 Hz, H-2'), 4.36 (dd, 1H, $J_{3',4'}$ 9.5 Hz, H-3'), 4.13 (dq, 1H, $J_{4',5'}$ 9.9, $J_{5',6'}$ 6.5 Hz, H-5'), 4.09 (s, 3H, OMe), 4,03 (s, 1H, HO-9), 3.24 (dd, 1H, $J_{8e,10e}$ 1.5 Hz, H-10e), 2.92 (d, 1H, $J_{10e,10ax}$ 18.9 Hz, H-10ax), 2.42 (s, 3H, H-14), 2.33 (apparent dt, 1H, $J_{8e,8ax}$ 15.7 Hz, H-8e) 2.17 (m, 1H, H-8ax), 2.06, 2.03 (t, 3H, OAc), 1.29 (d, 3H, H-6'); ¹³C-n.m.r.: $\delta$211.4 (C-13), 186.9, 186.7 (C-5, C-12), 169.7, 169.6 (C=O), 161.1 (C-4), 156.2, 155.6 (C-6, C-11), 135.7 (C-2), 135.5, 134.4, 133.1 (C-6a, C-10a, C-12a), 120.8 (C-4a), 119.9 (C-1), 118.5 (C-3), 111.5 (C-5a, C-11a), 104.8 (C-1'), 76.5 (C-9), 72.5 (C-4'), 70.9 (C-7), 69.1 (C-3'), 68.3 (C-5'), 56.7 (OMe), 35.3 (C-8), 33.3 (C-10), 29.6 (C-2'), 24.6 (C-14), 20.9, 20.8 (OAc), 17.5 (C-6').

Anal. Calc. for C₃₁H₃₁IO₁₃ (738.489): C, 50.42; H, 4.23; I, 17.18. Found: C, 50.20; H, 4.37; I, 17.39.

EXAMPLE 2

Preparation of 7-O-(3,4-di-O-acetyl-2,6-di-deoxy-2-iodo-α-L-talo-hexopyranosyl)daunomycinone (NSC 327472)

Daunomycinone (516 mg, 1.3 mmol) and 3,4-di-O-acetyl-L-fucal (352.4 mg, 1.65 mmol) were dissolved in a mixture of dry acetonitrile (10 mL) and tetrahydrofuran (5 mL). The mixture was vigorously stirred and cooled in an ice bath to 0°, and then N-iodosuccinimide (462.9 mg, 2.06 mmol) was added. After 15 minutes, the ice bath was removed and the mixture was stirred overnight at room temperature and then processed as in Example 1. The products were combined with the products of an exploratory reaction that started from 64 mg of daunomycinone and were chromatographed on a column of silica gel (25 g) with 4:1 benzene-acetone as eluant; yield 737 mg (77%), m.p. 131°, $[\alpha]_D^{23} + 64.9°$ (c 0.02, chloroform); $\nu_{max}^{KBr}$ 3510 (OH), 1748 (O-acetyl), 1720 (C-acetyl), 1621 and 1583 (chelated quinone), 1450, 1420, 1380, 1289, 1240, 1120, 1092, 1040, 995, 825, 798 and 771 cm$^{-1}$; $^1$H-n.m.r.: $\delta$14.00, 13.25 (s, 1H, HO-6, HO-11), 8.04 (dd, 1H, $J_{1,2}$ 7.7, $J_{1,3}$ 1.3 Hz, H-1), 7.79 (apparent t, 1H, H-2), 7.40 (dd, 1H, $J_{2,3}$ 7.3 Hz, H-3), 5.92 (bs, 1H, H-1'), 5.24 (m, 2H, H-4', H-7), 4.71 (dd, 1H, $J_{2',3'}$ 5.0, $J_{3',4'}$ 3.5 Hz, H-3'), 4.41 (qd, 1H, H-5'), 4.34 (dd, 1H, $J_{1',2'}$ 1.5 Hz, H-2'), 4.09 (s, 3H, OCH$_3$), 3.97 (s, 1H, HO-9), 3.23 (dd, 1H, $J_{8e, 10e}$ 1.7 Hz, H-10e), 2.94 (d, 1H, $J_{10e,10ax}$ 18.3 Hz, H-10 ax), 2.41 (s, 3H, H-14), 2.33 (m, 1H, H-8e), 2.14 (m, 1H, H-8ax), 2.21, 2.03 (s, 3H, OAc), 1.27 (d, 3H, $J_{5',6'}$ 6.45 Hz, H-6'); $^{13}$C-n.m.r.: $\delta$211.4 (C-13), 186.9, 186.8 (C-5, C-12), 170.4, 169.4 (C=O), 161.1 (C-4), 156.3, 155.6 (C-6, C-11), 135.7 (C-2), 135.5, 134.3, 133.2 (C-6a, C-10a, C-12a), 120.9 (C-4a), 119.9 (C-1), 118.6 (C-3), 111.6, 111.5 (c-5a, C-11a), 106.2 (C-1'), 76.4 (C-9), 70.9 (C-7), 68.1 (C-4'), 66.0 (C-5'), 65.8 (C-3'), 56.7 (OMe), 35.1 (C-8), 33.2 (C-10), 24.6 (C-14), 21.0 (C-2', OAc), 20.8 (OAc), 16.1 (C-6').

Anal. Calc. for C$_{31}$H$_{31}$IO$_{13}$.H$_2$O (756.593): C, 49.21; H, 4.40; I, 16.77. Found: C, 49.27; H, 4.83; I, 17.37.

We claim:

1. A compound selected from one member of the group of aglycons consisting of daunomycinone, desmethoxy daunomycinone, adriamycinone, and carminomycinone coupled at the 0–7 position to a 2'-halo α-L-hexopyranose sugar selected from the group of α-L-manno and α-L-talo at the 1' position of the sugar molecule according to the following formula:

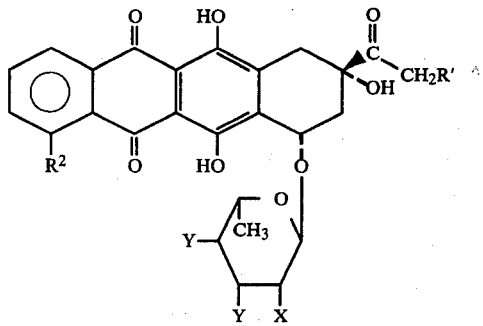

(1) R' = H; R$^2$ = OMe; X; Y
(2) R' = OH; R$^2$ = OMe; X; Y
(3) R' = H; R$^2$ = H; X; Y
(4) R' = H; R$^2$ = OH; X; Y
where: X = I, Cl, Br, or F and Y = OH or AcO(acetoxy)

(1) R'=H; R$^2$=OMe; X; Y
(2) R'=OH; R$^2$=OMe; X; Y
(3) R'=H; R$^2$=H; X; Y
(4) R'=H; R$^2$=OH; X; Y where:
X=I, Cl, Br, or F and
Y=OH or AcO (acetoxy).

2. The compound according to claim 1 wherein the aglycon utilized is daunomycinone.

3. The compound according to claim 1 wherein the aglycon utilized is desmethoxy daunomycinone.

4. The compound according to claim 1 wherein the aglycon utilized is adriamycinone.

5. The compound according to claim 1 wherein the aglycon utilized is carminomycinone.

6. The compound 7-O-(3,4-di-O-acetyl-2,6-dideoxy-2-iodo-α-L-manno-hexopyranosyl)daunomycinone

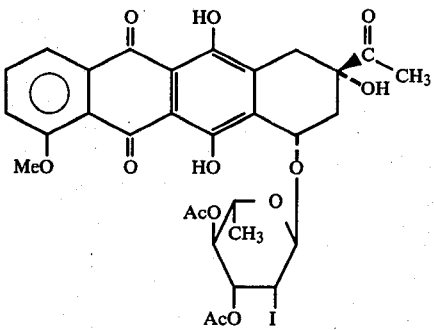

7. The compound 7-O-(3,4-di-O-acetyl-2,6-dideoxy-2-iodo-α-L-talo-hexopyranosyl)daunomycinone

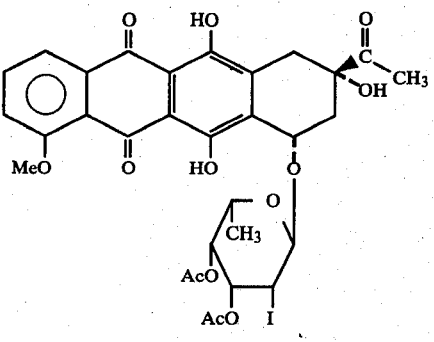

8. A method of treating murine leukemia in mice which comprises injecting a mouse infected with P388 leukemia with a biologically palliative amount and in a dosage regimen of up to 22 days of a compound selected from

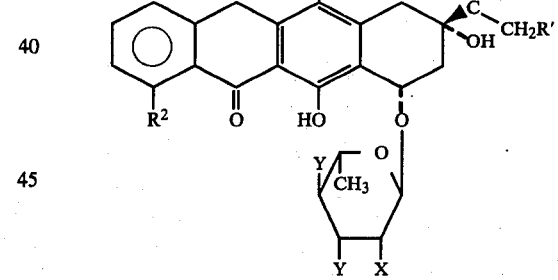

(1) R' = H; R$^2$ = OMe; X; Y
(2) R' = OH; R$^2$ = OMe; X; Y
(3) R' = H; R$^2$ = H; X; Y
(4) R' = H; R$^2$ = OH; X; Y
where: X = I, Cl, Br, or F; and Y = OH or AcO(acetoxy)

(1) R'=H; R$^2$=OMe; X; Y
(2) R'=OH; R$^2$=OMe; X; Y
(3) R'=H; R$^2$=H; X; Y
(4) R'=H; R$^2$=OH; X; Y
where:
X=I, Cl, Br, or F; and
Y=OH or AcO (acetoxy).

9. The method of claim 8 wherein the aglycon utilized is daunomycinone.

10. The method of claim 8 wherein the aglycon utilized is desmethoxy daunomycinone.

11. The method of claim 8 wherein the aglycon utilized is adriamycinone.

12. The method of claim 8 wherein the aglycon utilized is carminomycinone.

* * * * *